United States Patent [19]
Jones et al.

[11] Patent Number: 5,847,138
[45] Date of Patent: Dec. 8, 1998

[54] CHEMICAL PROCESS

[75] Inventors: John David Jones, Bury; Gareth Andrew DeBoos, Ramsbottom; Paul Wilkinson, Blacklet; Brian Geoffrey Cox, Poynton; Jan Michael Fielden, Bury, all of England

[73] Assignee: Imperial Chemical Industries PLC, London, England

[21] Appl. No.: 479,242

[22] Filed: Jun. 7, 1995

Related U.S. Application Data

[63] Continuation of Ser. No. 116,438, Sep. 3, 1993, abandoned, which is a continuation of Ser. No. 788,078, Nov. 5, 1991, abandoned.

[30] Foreign Application Priority Data

| Nov. 16, 1990 | [GB] | United Kingdom | 9024960 |
| Nov. 16, 1990 | [GB] | United Kingdom | 9024992 |
| May 16, 1991 | [GB] | United Kingdom | 9110592 |
| Jun. 14, 1991 | [GB] | United Kingdom | 9112832 |
| Jun. 14, 1991 | [GB] | United Kingdom | 9112833 |
| Jun. 27, 1991 | [GB] | United Kingdom | 9113911 |
| Jun. 27, 1991 | [GB] | United Kingdom | 9113914 |

[51] Int. Cl.$^6$ .................. C07D 239/34; C07D 239/52
[52] U.S. Cl. ........................... 544/319; 544/298
[58] Field of Search ................... 544/298, 319

[56] References Cited

FOREIGN PATENT DOCUMENTS

| 0 178 826 | 4/1986 | European Pat. Off. |  |
| 0393861 | 10/1990 | European Pat. Off. | 544/319 |

*Primary Examiner*—Yogendra N. Gupta
*Attorney, Agent, or Firm*—Marian T. Thomson

[57] ABSTRACT

A process for the preparing agrochemical intermediates of formula (I):

(I)

wherein W is $(CH_3O)CH.CHCO_2CH_3$ or $CH_3O.CH=CCO_2CH_3$; $Z^1$ is a halogen atom; and $R^1$, $R^2$, $R^3$ and $R^4$ are independently hydrogen, halogen, $C_{1-4}$ alkyl, $C_{1-4}$ alkoxy, acetoxy or acyl; the process comprising the steps of:

(a) reacting a compound of formula (II):

(II)

wherein X, $R^1$, $R^2$, $R^3$ and $R^4$ are as defined above, with a compound of formula $ROCH_3$, wherein R is a metal; and, (b) reacting the product of (a) with a compound of formula (III):

(III)

wherein $Z^1$ and $Z^2$ are halogen atom.

A process for the preparation of compounds of formula (II) and compounds of formula (II) themselves. A process for obtaining, in substantially pure form, a compound of formula (II) wherein $R^1$, $R^2$, $R^3$ and $R^4$ are all hydrogen.

16 Claims, No Drawings

CHEMICAL PROCESS

This application is a continuation of application Ser. No. 08/116,438, filed Sep. 3, 1993 abandoned, which is a continuation of application Ser. No. 07/788,078, filed Nov. 5, 1991.

This invention relates to a process for the preparation of phenoxypyrimidine compounds that can be used as intermediates in the preparation of fungicides, to methods for preparing 3-(α-methoxy)methylenebenzofuranones which are intermediates in said process, to certain 3-(α-methoxy) methylenebenzofuranones, to a process for obtaining substantially pure 3-(α-methoxy)methylenebenzofuran-2(3H)-one from its mixture with other compounds and intermediates in this process, and the preparation of 3-formylbenzofuran-2(3H)-one.

It is known that 3-(α-methoxy)methylenebenzofuran-2 (3H)-one can be made by methylation of 3-formylbenzofuran-2(3H)-one with either diazomethane or methanolic sulphuric acid [J. A. Elix and B. A. Ferguson in *Australian Journal of Chemistry* 26(5) 1079–91 (1973)].

Attempts to formylate benzofuran-2(3H)-one are reported to have been unsuccessful [A. D. Harmon and C. R. Hutchinson in *Journal of Organic Chemistry* 40(24) 3474–3480 (1975)].

According to the present invention there is provided a process for the preparation of a compound of formula (I), wherein W is $(CH_3O)_2CH.CHCO_2CH_3$ or $CH_3O.CH=CCO_2CH_3$; $Z^1$ is a halogen atom; and $R^1$, $R^2$, $R^3$ and $R^4$ are independently hydrogen, halogen, $C_{1-4}$ alkyl, $C_{1-4}$ alkoxy, acetoxy or acyl; the process comprising the steps of:

(a) reacting a compound of formula (II), wherein $R^1$, $R^2$, $R^3$ and $R^4$ are as defined above, with a compound of formula $ROCH_3$, wherein R is a metal; and, (b) reacting the product of (a) with a compound of formula (III), wherein $Z^1$ and $Z^2$ are halogen atoms.

In one aspect the present invention provides a process for the preparation of a compound of general formula (IV), wherein $Z^1$ is a halogen atom (preferably chlorine); the process comprising reacting a compound of formula (X) with a compound of general formula (III), wherein $Z^1$ is as defined above and $Z^2$ is a halogen atom (preferably chlorine), in the presence of a methoxide anion and optionally another suitable base.

In a further aspect the present invention provides a process for the preparation of a compound of general formula (IV), wherein $Z^1$ is a halogen atom (preferably chlorine); the process, which is carried out in the presence of methanol, comprising the steps of:

(a) reacting a compound of formula (X) with a compound of formula $ROCH_3$, wherein R is a metal, and optionally another suitable base; and (b) reacting the product of (a) with a compound of general formula (III), wherein $Z^1$ is as defined above and $Z^2$ is a halogen atom (preferably chlorine).

In another aspect the present invention provides a process for the preparation of a compound of general formula (V), wherein $Z^1$ is a halogen atom (preferably chlorine), the process comprising the steps of:

a) reacting a compound of formula (X) with a compound of formula $ROCH_3$, wherein R is a metal, and optionally another suitable base; and, b) reacting the product of (a) with a compound of formula (III) wherein $Z^1$ is as defined above and $Z^2$ is a halogen atom (preferably chlorine).

In yet another aspect the invention provides a process for the preparation of a compound of formula (I), wherein W, $Z^1$, $R^1$, $R^2$, $R^3$ and $R^4$ are as defined above, the process comprising the steps of:

a) reacting a compound of formula (II), wherein $R^1$, $R^2$, $R^3$ and $R^4$ are as defined above, with a compound of formula $ROCH_3$, wherein R is a metal;

b) reacting the product of (a) with a compound of formula (III), wherein $Z^1$ and $Z^2$ are as defined above; step (b) being carried out in the presence of methanol.

In a further aspect the invention provides a process for the preparation of a compound of formula (V), comprising reacting a compound, obtainable by reacting a compound of formula (II) with a compound of formula $ROCH_3$ (wherein R is a metal), with a compound of formula (III).

In another aspect the present invention provides a process for the preparation of a compound of formula (IV), the process, which is carried out in the presence of methanol, comprising reacting a compound, obtainable by reacting a compound of formula (II) with a methoxide anion (preferably from a compound of formula $ROCH_3$, wherein R is a metal) in the presence of methanol, with a compound of formula (III).

The process of the present invention normally produces compounds of formula (I) as a mixture of acetal (wherein W is $(CH_3O)_2CHCHCO_2CH_3$) and acrylate (wherein W is $CH_3O.HC=CCO_2CH_3$). (The proportion of acetal to acrylate is dependent on a number of factors including the nature of solvent used. Examples of solvents are given in Table 1.) Thus, in a further aspect, the present invention provides a process for the preparation of a mixture of compounds of formula (I) wherein W is $(CH_3O)_2CHCHCO_2CH_3$ and $CH_3O.HC=CCO_2CH_3$, and wherein $Z^1$, $R^1$, $R^2$, $R^4$ are as defined above; the process, which is optionally carried out in the presence of methanol, comprising the steps of:

(a) reacting a compound of formula (II) with a compound of $ROCH_3$, wherein R is a metal; and, (b) reacting the product of (a) with a compound of formula (III) wherein $Z^1$ is as defined above and $Z^2$ is a halogen atom (preferably chlorine).

In a further aspect the process of the present invention produces a mixture of compounds of formulae (IV) and (V) in between the range of ratios 100:0 to 2:98 of (IV):(V), especially 99:1 to 25:75 of (IV):(V), more especially 97:3 to 32:68 of (IV):(V) (for example, 90:10 to 70:30 of (IV):(V)).

In another aspect the present invention provides a process for the preparation of a mixture of compounds of formulae (IV) and (V), wherein $Z^1$ is as defined above, in the range of ratios 100:0 to 2:98 of (IV):(V), the process, which is carried out in the presence of methanol, comprising the steps of:

(a) reacting a compound of formula (X) with a compound of formula $ROCH_3$, wherein R is a metal, and optionally another suitable base; and (b) reacting the product of (a) with a compound of general formula (III), wherein $Z^1$ and $Z^2$ are as defined above.

In a further aspect the present invention provides a process for the preparation of a compound of formula (V), the process comprising the steps of:

a) reacting a compound of formula (X) with a compound of formula $ROCH_3$, wherein R is a metal, and optionally another suitable base;

b) reacting the product of (a) with a compound of formula (III) to produce a compound of formula (IV); and, c) eliminating methanol from the compound of formula (IV) using a suitable method;

steps (a) and (b) being carried out in the presence of methanol.

In another aspect the present invention provides a process for the preparation of a compound of formula (V), wherein $Z^1$ is as defined above, the process comprising the steps of:
  a) reacting a compound of formula (X) with a compound of formula $ROCH_3$ and optionally another suitable base;
  b) reacting the product of (a) with a compound of formula (III) to produce a mixture of compounds of formulae (IV) and (V) in the range of ratios 100:0 to 2:98 of (IV):(V); and,
  c) eliminating methanol from the compound of formula (IV) of said mixture using a suitable method, thereby producing substantially pure (V) from said mixture;
steps (a) and (b) being carried out in the presence of methanol.

The present invention also provides the product of the process comprising reacting a compound of formula (X) with a compound of formula $ROCH_3$, wherein R is a metal.

The present invention further provides the product of the process comprising reacting a compound of formula (X) with a compound of formula $ROCH_3$, wherein R is a metal, in the presence of methanol.

In another aspect the present invention provides a process for the preparation of a compound of formula (VI) and stereoisomers thereof, wherein $R^1$, $R^2$, $R^3$ and $R^4$ are as defined above; and Y and Z are, independently, hydrogen, halogen, cyano, $C_{1-4}$ alkyl, $C_{1-4}$ haloalkyl, $C_{1-4}$ alkoxy, $C_{1-4}$ halolakoxy, $CSNH_2$, $CONH_2$ or nitro; the process comprising the steps of:
  (a) reacting a compound of formula (II) with a compound of formula $ROCH_3$;
  (b) reacting the product of (a) with a compound of formula (III); and
  1) (c) eliminating methanol from the compound of formula (I), wherein W is $(CH_3O)_2CHCHCO_2CH_3$, in the mixture of products from (b); and
    (d) reacting the product of (c) with a compound of formula (VII), wherein Z and Y are as defined above; OR
  2) (c) reacting the product of (b) with a compound of formula (VII), wherein Z and Y are as defined above; and
    (d) (i) separating the compound of formula (VI); or
      (ii) eliminating methanol from a compound of formula (VIII), wherein $R^1$, $R^2$, $R^3$, $R^4$, Y and Z are as defined above, in the mixture of products from (c); or
      (iii) separating the compound of formula (VIII) from the mixture of products from (c) and eliminating methanol from it; OR
  3) (c) separating the compounds of formula (I), wherein W is $(CH_3O)_2CHCHCO_2CH_3$ and $CH_3O.CH=CCO_2CH_3$, in the mixture of products from (b); and
    (d) (i) reacting the compound of formula (I), wherein W is $CH_3O.CH=CCO_2CH_3$, with a compound of formula (VII), wherein Y and Z are defined above; or
      (ii) reacting the compound of formula (I), wherein W is $(CH_3O)_2CHCHCO_2CH_3$, with a compound of formula (VII); and eliminating methanol from the product so formed; or
      (iii) eliminating methanol from the compound of formula (I), wherein W is $(CH_3O)_2CHCHCO_2CH_3$, and reacting the product so formed with a compound of formula (VII) wherein Y and Z are as defined above.

In a further aspect the present invention provides a process for the preparation of a compound of formula (VI), wherein Z and Y are independently hydrogen, halogen, cyano, $C_{1-4}$ alkyl, $C_{1-4}$ haloalkyl, $C_{1-4}$ alkoxy, $C_{1-4}$ haloalkoxy, $CSNH_2$, $CONH_2$ or nitro; and $R^1$, $R^2$, $R^3$ and $R^4$ are hydrogen; the process comprising the steps of:
  a) reacting a compound of formula (X) with a compound of formula $ROCH_3$, wherein R is a metal, and optionally another suitable base;
  b) reacting the product of (a) with a compound of formula (III) to produce a compound of formula (V); and,
  c) reacting the compound of formula (V) with a phenol of formula (VII), wherein Z and Y are as defined above, in the presence of a base.

In a further aspect the present invention provides a process for the preparation of a compound of formula (VI), wherein Z and Y are independently hydrogen, halogen, cyano, $C_{1-4}$ alkyl, $C_{1-4}$ haloalkyl, $C_{1-4}$ alkoxy, $C_{1-4}$ haloalkoxy, $CSNH_2$, $CONH_2$ or nitro; and $R^1$, $R^2$, $R^3$ and $R^4$ are hydrogen; the process comprising the steps of:
  a) reacting a compound of formula (X) with a compound of formula $ROCH_3$ and optionally another suitable base;
  b) reacting the product of (a) with a compound of formula (III) to produce a compound of formula (IV); and
  c) reacting the compound of formula (IV) with a phenol of formula (VII), wherein Z and Y are as defined above, in the presence of a base;
steps (a) and (b) being carried out in the presence of methanol.

In a still further aspect the present invention provides a process for the preparation of a compound of formula (VI), wherein Z and Y are independently hydrogen, halogen, cyano, $C_{1-4}$ alkyl, $C_{1-4}$ haloalkyl, $C_{1-4}$ alkoxy, $C_{1-4}$ haloalkoxy, $CSNH_2$, $CONH_2$ or nitro; and $R^1$, $R^2$, $R^3$ and $R^4$ are hydrogen; the process comprising the steps of:
  a) reacting a compound of formula (X) with a compound of formula $ROCH_3$ and optionally another suitable base;
  b) reacting the product of (a) with a compound of formula (III) to produce a mixture of compounds of formulae (IV) and (V) in the range of ratios 100:0 to 2:98 of (IV):(V); and
  c) reacting said mixture with a phenol of formula (VII) in the presence of a base;
steps (a) and (b) being carried out in the presence of methanol.

In yet another aspect the present invention provides a process for the preparation of a compound of formula (VI), wherein Z and Y are independently hydrogen, halogen, cyano, $C_{1-4}$ alkyl, $C_{1-4}$ haloalkyl, $C_{1-4}$ alkoxy, $C_{1-4}$ haloalkoxy, $CSNH_2$, $CONH_2$ or nitro; and $R^1$, $R^2$, $R^3$ and $R^4$ are hydrogen; the process comprising the steps of:
  a) reacting a compound of formula (X) with a compound of formula $ROCH_3$ and optionally another suitable base;
  b) reacting the product of (a) with a compound of formula (III) to produce a compound of formula (IV);
  c) eliminating methanol from the compound of formula (IV) using a suitable method to produce a compound of formula (V); and,
  d) reacting the compound of formula (V) with a phenol of formula (VII) in the presence of a base;
steps (a) and (b) being carried out in the presence of methanol.

In a still further aspect the present invention provides a process for the preparation of a compound of formula (VI), wherein Z and Y are independently hydrogen, halogen, cyano, $C_{1-4}$ alkyl, $C_{1-4}$ haloalkyl, $C_{1-4}$ alkoxy, $C_{1-4}$ haloalkoxy, $CSNH_2$, $CONH_2$ or nitro; and $R^1$, $R^2$, $R^3$ and $R^4$ are hydrogen; the process comprising the steps of:
  a) reacting a compound of formula (X) with a compound of formula $ROCH_3$ and optionally another suitable base;
  b) reacting the product of (a) with a compound of formula (III) to produce a mixture of compounds of formulae (IV) and (V) in the range of ratios 100:0 to 2:98 of (IV):(V);
  c) eliminating methanol from the compound of formula (IV) in said mixture using a suitable method to produce the compound of formula (V) in a substantially pure state from said mixture; and,
  d) reacting the compound of formula (V) with a phenol of formula (VII) in the presence of a base;
steps (a) and (b) being carried out in the presence of methanol.

In a further aspect the present invention provides a process for the preparation of a compound of formula (I), the process comprising the steps of:
  i) (a) reacting a compound of formula (XIV), wherein $R^1$, $R^2$, $R^3$ and $R^4$ are as defined above, with trimethyl orthoformate;
    (b) reacting the product of (a) with a compound of formula $ROCH_3$, wherein R is a metal; and,
    (c) reacting the product of (b) with a compound of formula (III); or
  ii) (a) reacting a compound of formula (XIV) wherein $R^1$, $R^2$, $R^3$ and $R^4$ are as defined above, with a dimethoxymethyl carboxylate;
    (b) reacting the product of (a) with a compound of formula $ROCH_3$, wherein R is a metal; and,
    (c) reacting the product of (b) with a compound of formula (III); or
  iii) (a) cyclising a compound of formula (IX) and reacting the product formed with either trimethyl orthorformate or a dimethoxymethyl carboxylate;
    (b) reacting the product of (a) with a compound of formula $ROCH_3$, wherein R is a metal; and,
    (c) reacting the product of (b) with a compound of formula (III).

In a still further aspect the present invention provides a process for the compound of formula (VI), and stereoisomers thereof, wherein Z and Y are independently hydrogen, halogen, cyano, $C_{1-4}$ alkyl, $C_{1-4}$ haloalkyl, $C_{1-4}$ alkoxy, $C_{1-4}$ haloalkoxy, $CSNH_2$, $CONH_2$ or nitro; and $R^1$, $R^2$, $R^3$ and $R^4$ are as defined above; the process comprising the steps of:
  1) forming a compound of formula (X), and stereoisomers thereof, by:
    i) reacting a compound of formula (XIII) with trimethyl orthoformate (preferably in the presence of an activating agent such as an acid anhydride); or
    ii) reacting a compound of formula (XVII) with an acid anhydride and trimethyl orthoformate at a suitable temperature; or
    iii) cyclising a compound of formula (XVII) and reacting the product so formed with trimethyl orthoformate (preferably in the presence of an activating agent such as an acid anhydride); or
    iv) reacting a mixture of compounds of formulae (XIII) and (XVII) with an acid anhydride and trimethyl orthoformate; or
    v) reacting a compound of formula (XIII) with a dimethoxymethyl carboxylate (such as dimethoxymethyl acetate);
  2) a) reacting the compound of formula (X) with a compound of formula $ROCH_3$ and optionally another suitable base; and
    b) reacting the product of (2)(a) with a compound of general formula (III), wherein $Z^1$ and $Z^2$ are as defined above, to give a mixture of compounds (IV) and (V), in the range of ratios 100:0 to 2:98 of (IV):(V); and either
  3) a) treating the mixture of compounds (IV) and (V) using a suitable method to eliminate methanol from the compound of formula (IV) and hence produce substantially pure (V) from said mixture; and,
    b) reacting the substantially pure (V) with a phenol of formula (VII), wherein Z and Y are as defined above, in the presence of a base, to give a compound of formula (VI) as defined above; or
  4) reacting the mixture of compounds (IV) and (V), or a compound of formula (IV), with a phenol of formula (III), wherein Z and Y are as defined above, in the presence of a base to give a compound of formula (VI) as defined above;
steps (2)(a) and (2)(b) being carried out in the presence of methanol.

In a further aspect the present invention provides a process for the preparation of a compound of formula (VI), and stereoisomers thereof, wherein Z, Y, $R^1$, $R^2$, $R^3$ and $R^4$ are as defined above, the process comprising the steps of:
  1) forming a compound of formula (X), and stereoisomers thereof, by:
    i) reacting a compound of formula (XIII) with trimethyl orthoformate (preferably in the presence of an activating agent such as an acid anhydride); or
    ii) reacting a compound of formula (XVII) with an acid anhydride and trimethyl orthoformate at a suitable temperature; or
    iii) cyclising a compound of formula (XVII) and reacting the product so formed with trimethyl orthoformate (preferably in the presence of an activating agent such as an acid anhydride); or
    iv) reacting a mixture of compounds of formulae (XIII) and (XVII) with an acid anhydride and trimethyl orthoformate; or
    v) reacting a compound of formula (XIII) with a dimethoxymethyl carboxylate (such as dimethoxymethyl acetate);
  2) a) reacting the compound of formula (X) with a compound of formula $ROCH_3$ (wherein R is a metal) and optionally another suitable base; and,
    b) reacting the product of (2)(a) with a compound of general formula (III), wherein $Z^1$ and $Z^2$ are as defined above, to give a compound of formula (V); and,
  3) reacting (V) with a phenol of formula (VII), wherein Z and Y are as defined above, in the presence of a base.

In all of the foregoing processes it is preferred that the molar ratio of a compound of formula (II) or (X) to a compound of formula (III) is in the range 2:1 to 1:1, more preferably in the range 1.5:1 to 1:1.

In another aspect the present invention provides a process for the preparation of a compound of formula (II), wherein $R^1$, $R^2$, $R^3$ and $R^4$ are independently hydrogen, halogen, $C_{1-4}$ alkyl, $C_{1-4}$ alkoxy, acetoxy or acyl; the process comprising:
  i) reacting a compound of formula (XIV), wherein $R^1$, $R^2$, $R^3$ and $R^4$ are as defined above, with trimethyl orthoformate; or
  ii) (a) cyclising a compound of formula (IX), wherein $R^1$, $R^2$, $R^3$ and $R^4$ are as defined above, and (b) reacting the product so formed with either trimethyl orthorformate or a dimethoxymethyl carboxylate; or iii) reacting a compound of formula (IX), wherein $R^1$, $R^2$, $R^3$ and $R^4$ are as defined above, with an acid anhydride and trimethyl orthoformate at a suitable temperature; or iv) reacting a compound of formula (XIV) wherein $R^1$, $R^2$, $R^3$ and $R^4$ are as defined above, with a dimethoxymethyl carboxylate.

According to the present invention there is provided a process for the preparation of 3-(α-methoxy)methylenebenzofuranones having the general formula (II) and stereoisomers thereof, wherein $R^1$, $R^2$, $R^3$ and $R^4$ independently hydrogen, halogen, $C_{1-4}$ alkyl, $C_{1-4}$ alkoxy or acyl; the process comprising reacting a compound of formula (XIV), wherein $R^1$, $R^2$, $R^3$ and $R^4$ are as defined above, with trimethyl orthoformate. It is preferred that this reaction is conducted in the presence of an activating agent such as an acid anhydride.

In another aspect the present invention provides a process for the preparation of a compound of general formula (II); the process comprising the steps of:

a) cyclising a compound of formula (IX), and, b) reacting the product so formed with a trimethyl orthoformate.

It is preferred that the reaction in step (b) is conducted in the presence of an activating agent such as an acid anhydride. The invention includes steps (a) and (b) individually or in combination.

In a further aspect the present invention provides a process for the preparation of a compound of general formula (II); the process comprising reacting a mixture of compounds of formulae (IX) and (XIV) with trimethyl orthoformate and an acid anhydride at a suitable temperature.

In yet another aspect the present invention provides a process for the preparation of a compound of general formula (II); the process comprising reacting a compound of formula (IX) with an acid anhydride and trimethyl orthoformate at a suitable temperature.

The compound of formula $ROCH_3$ (wherein R is a metal, preferably an alkali metal, for example sodium or potassium) is a source of methoxide anion. The compound of formula $ROCH_3$ is, for example, sodium methoxide.

The methoxide anion is the anion $CH_3O^-$ and it is preferred that the anion is present in the form of an alkali metal (for example sodium) methoxide.

It is preferred that the compound of formula (VI) has the variables Z and Y selected form the group comprising hydrogen, fluorine, cyano, $CSNH_2$, $CONH_2$ and nitro.

The alkyl moiety and the alkyl moieties of alkoxy, haloalkyl and haloalkoxy are either a straight or branched chain and are, for example, methyl, ethyl, n-propyl, iso-propyl, n-butyl or tert-butyl.

Halogen inludes fluorine, bromine and iodine but is preferably chlorine.

Acyl includes carbacyl which includes $C_{1-6}$ alkanoyl (for example acetyl) and benzoyl (wherein the phenyl moiety is optionally substituted by halogen, $C_{1-4}$ alkoxy or $C_{1-4}$ alkyl).

The compounds of general formulae (I) (when W is $CH_3O.HC=CCO_2CH_3$), (II), (V), (VI), (X), (XI) and (XII) can exist in the form of two geometric isomers, referred to as (E)- and (Z)-isomers. The processes of the present invention predominantly produce (E)-isomers.

It is preferred that, where reactions are carried out in the presence of methanol, methanol is present in the range 0.5 to 8 equivalents, preferably 0.5 to 6 equivalents, for example 1 to 4 equivalents.

In all of the foregoing processes it is preferred that $R^1$, $R^2$, $R^3$ and $R^4$ are all hydrogen.

In a further aspect the invention provides a compound of formula (II) wherein $R^1$, $R^2$, $R^3$ and $R^4$ are independently hydrogen, halogen, $C_{1-4}$ alkyl, $C_{1-4}$ alkoxy, acetoxy or acyl, but are not all hydrogen.

The foregoing processes of the invention are shown diagrammatically in Scheme I. Throughout Scheme I the variables Z, $Z_1$, $Z_2$, Y, $R^1$, $R^2$, $R^3$ and $R^4$ are as defined above.

A compound of formula (II) can be prepared by reacting a compound of formula (XIV) with trimethyl orthoformate in a suitable solvent (for example trimethyl orthoformate or an inert solvent such as a hydrocarbon solvent, for example toluene), at a suitable pressure, preferably in the range 1–5 atmospheres, usually atmospheric pressure, and at a suitable temperature (preferably in the range 20°–180° C., suitably 90°–130° C. (for example 95°–110° C.)). It is preferred that an acid anhydride (preferably an alkyl acid anhydride (for example acetic anhydride or iso-butyric anhydride)) is used with the trimethyl orthoformate in this reaction, and in this case the suitable solvent can be the acid anhydride, trimethyl orthoformate, or a mixture of the two and/or an inert solvent such as a hydrocarbon solvent, for example toluene.

Alternatively, a compound of formula (II) can be prepared by a 2-step process. The first step comprises cyclising a compound of formula (IX), suitably by heating it, preferably in the presence of another suitable acid (for example glacial acetic acid) which is preferably present in a catalytic amount, optionally in a suitably high boiling point and inert solvent (such as a hydrocarbon solvent (for example toluene or a xylene)) at a suitable temperature, preferably 20°–250° C., suitably 50°–200° C., for example 90°–150° C., and at a suitable pressure in the range 0.1–10 atmospheres, preferably at atmospheric or autogenic pressure. It is preferred that when a solvent is used, the temperature at which this cyclisation is carried out is the boiling point of said solvent or its azeotrope with water. It is further preferred that any water generated by the cyclisation is removed during the course of the reaction.

The second step comprises reacting the product of cyclisation of the compound of formula (IX) with trimethyl orthoformate in a suitable solvent (for example trimethyl orthoformate and/or an inert soluent such as a hydrocarbon solvent, for example toluene) and at a suitable temperature (preferably 20°–180° C., suitably 90°–130° C., for example 95°–110° C.) to give a compound of formula (II). It is further preferred that an acid anhydride (preferably an alkyl acid anhydride (for example acetic anhydride or iso-butyric anhydride)) is used with the trimethyl orthoformate in this reaction. In this case the suitable solvent can be the acid anhydride or a mixture of trimethyl orthoformate and the acid anhydride.

It is probable that the product of the cyclisation of a compound of formula (IX) is a compound of formula (XIV). The two steps of this 2-step process can be combined in a "one-pot" process.

Alternatively the compound of formula (II) can be prepared by reacting a compound of formula (IX) with an acid anhydride (preferably an alkyl acid anhydride (for example acetic anhydride or iso-butyric anhydride)) and trimethyl orthoformate, optionally in a suitable solvent (for example acetic anhydride or trimethyl orthoformate or a mixture of the two and/or optionally an inert solvent such as a hydrocarbon solvent, for example toluene or a xylene), at a suitable temperature (preferably 20°–250° C., suitably 50°–200° C., for example 90°–150° C.), and at a suitable pressure in the range 0.1–10 atmospheres, preferably at atmospheric or autogenic pressure.

Alternatively the compound of general formula (II) can be prepared by reacting a mixture of compounds of formulae (XIV) and (IX) with trimethyl orthoformate and an acid anhydride (preferably an alkyl acid anhydride (for example, acetic anhydride or iso-butyric anhydride)), optionally in a suitable solvent (for example, acetic anhydride or trimethyl orthoformate or a mixture of the two or a mixture of one or both with an inert solvent such as a hydrocarbon solvent, for example toluene or a xylene), at a suitable temperature (preferably 20°–250° C., suitably 50°–200° C. for example 90°–150° C.) and at a suitable pressure, preferably in the range 0.1–10 atmospheres, usually atmospheric or autogenic pressure.

Under suitable conditions an acid anhydride (for example acetic anhydride) can react with trimethyl orthoformate to form a dimethoxymethyl carboxylate (for example dimethoxymethyl acetate). Therefore, in another alternative, a compound of formula (II) can be prepared by reacting a compound a compound of formula (XIV) with a dimethoxymethyl carboxylate (preferably dimethoxymethyl acetate) at a suitable temperature, preferably in the range 20°–180° C., suitably 90°–130° C. (for example 95°–100° C.). In another aspect the present invention provides a process for the preparation of a compound of formula (II), and stereoisomers thereof, the process comprising reacting a compound of formula (XIV) with a dimethoxymethyl carboxylate at a suitable temperature, preferably in the range 20°–180° C., suitably 90°–130° C. (for example 95°–110° C.).

For all processes for the preparation of the compound of formula (II) it is preferred that the apparatus in which the process is carried out is adapted to allow the removal of volatile by-products.

The compound of formula (X) is 3-(α-methoxy)-methylenebenzofuran-2(3H)-one.

Compounds of formula (IX) can be made by standard literature methods. In addition to the methods described above for the prepartion of compounds (XIV) from compounds (IX), compounds (XIV) can be made by methods described in the literature.

Compounds of general formula (VI) can be prepared by reacting a compound of formula (I), wherein W is $CH_3O.CH=CCO_2CH_3$ with a phenol of general formula (VII), wherein Z and Y are as defined above, in the presence of a suitable base (preferably an alkali metal (for example sodium or potassium) carbonate), optionally in the presence of a suitable copper catalyst (for example a copper halide (preferably cuprous chloride)) in a suitable solvent (preferably polar, for example N,N-dimethylformamide) and at a suitable temperature (preferably in the range 0°–150° C., for example 40°–130° C.).

A compound of formula (I), wherein W is $CH_3O.HC=CCO_2CH_3$, can be prepared by using a suitable method to eliminate methanol from a compound of formula (I), wherein W is $(CH_3O)_2CHCHCO_2CH_3$. It is preferred that the method of eliminating methanol from the compound of formula (I) wherein W is $(CH_3O)_2CHCHCO_2CH_3$, and which can be in admixture with a compound of formula (I) wherein W is $CH_3O.CH=CCO_2CH_3$ involves heating said compound or mixture to a temperature in the range 60°–300° C., optionally in the presence of a suitable catalyst, preferably an acid catalyst [for example potassium bisulphate (where temperatures in the range 100°–300° C., preferably 140°–300° C. (for example 160°–250° C.), more preferably 140°–160° C. are more suitable) or p-toluene sulphonic acid (where temperatures in the range 80°–300° C., preferably 80°–160° C. are more suitable)], optionally under a reduced pressure (suitably 1–50 mm Hg, for example 5–30 mm Hg) and optionally in the presence of a suitable solvent.

Alternatively, elimination of methanol from the compound of formula (I) wherein W is $(CH_3O)_2CHCHCO_2CH_3$ when it is alone or in a mixture with a compound of formula (I) wherein W is $CH_3 O.CH=CCO_2CH_3$, can be effected by an acidic work-up when the compound or mixture is prepared, followed by heating the compound or mixture to a temperature in the range 100°–300° C., preferably 140°–300° C. (for example 160°–250° C.), more preferably 140°–160° C., optionally under a reduced pressure (suitably 1–50 mm Hg, for example 5–30 mm Hg).

A mixture of compounds of formulae (I) wherein W is $(CH_3O)_2CHCHCO_2CH_3$ and $CH_3O.CH=CCO_2CH_3$ can be prepared by reacting a compound of formula (II), with a compound of formula $ROCH_3$ (preferably sodium methoxide) and optionally another suitable base, and reacting the product so formed with a compound of general formula (III), wherein $Z^1$ and $Z^2$ are as defined above; both stages optionally being carried out in the presence of methanol, in a suitable solvent (preferably an ether (for example tetrahydrofuran, tert-butyl ether or diethyl ether), a methyl ester (for example ($C_{1-4}$ alkyl)$CO_2CH_3$) an aromatic hydrocarbon (for example xylene or toluene), acetonitrile, pyridine, a chlorinated hydrocarbon (for example carbon tetrachloride), diethoxymethane or methylisobutyl ketone) and at a suitable temperature (preferably in the range −10°–100° C., for example 0°–50° C.). The compounds of formulae (I) can be isolated from the mixture of these two compounds using standard techniques (for example chromatography).

Alternatively, compounds of general formula (I) can be prepared by reacting a mixture of compounds of formula (I) wherein W is $(CH_3O)_2CHCHCO_2CH_3$ and $CH_3O.CH=CCO_2CH_3$, or a compound of formula (I), wherein W is $(CH_3O)_2CHCHCO_2CH_3$ with a phenol of general formula (VII), wherein Z and Y are as defined above, in the presence of a suitable base (preferably an alkali metal (for example sodium or potassium) carbonate), optionally in the presence of a suitable copper catalyst (for example a copper halide (preferably cuprous chloride)) in a suitable solvent (preferably polar, for example N,N-dimethylformamide) and at a suitable temperature (preferably in the range 0°–150° C., for example 40°–130° C.).

A compound of formula (X) is used in the processes for preparing of compounds of formulae (IV) and (V). On completion of these processes some compound of formula (X) might remain in the reaction mixture and it is desirable to be able to isolate this for use in other reactions.

The present invention provides a process for obtaining, in a substantially pure form, a compound of formula (X) from a mixture comprising a compound of formula (X), an acetal and an acrylate, the process comprising the steps of:

α) contacting an aqueous solution of a base and said mixture to produce a compound of formula (XI), wherein M is an alkali metal or an alkaline earth metal and n is 1 or 2;

β) contacting the product of step (α) with an acid to produce a compound of formula (XII); and, γ) reacting the product of step (β) with methanol in the presence of a strong acid;

and separating a compound of formula (XI) or (XII) at step (α) or (β).

In one aspect the present invention provides a compound of general formula (XI) wherein M is an alkali metal (especially sodium or potassium) or an alkaline earth metal (especially calcium or magnesium) and n is 1 or 2 (depending upon valency requirements).

In a further aspect the present invention provides a process for obtaining, in a substantially pure form, a compound of formula (X) from a mixture comprising a compound of formula (X), an acetal and an acrylate, the process comprising the steps of:

α) contacting an aqueous solution of an alkali metal hydroxide and said mixture to produce a compound of formula (XI), wherein M is an alkali metal (for example sodium or potassium, but preferably sodium) or an alkaline earth metal (for example calcium) and n is 1 or 2;

β) contacting the product of step (α) with an acid to produce a compound of formula (XII); and, γ) reacting the product of step (β) with methanol in the presence of a strong mineral acid;

and separating a compound of formula (XI) or (XII) at step (α) or (β).

In step (α) the base can be an alkaline earth metal (for example calcium) carbonate or hydroxide, but is preferably an alkali metal carbonate or hydroxide (for example sodium hydroxide or potassium hydroxide).

In step (β) the acid can be an organic acid (for example acetic acid), but is preferably a mineral acid (for example hydrochloric acid or sulphuric acid).

In step (γ) the strong acid is preferably a stong mineral acid (for example sulphuric acid or hydrochloric acid).

Compounds of formulae (XI) and (XII) appear, from their nuclear magnetic resonance spectra, to exist primarily in an enolic form. The process for obtaining, in a substantially pure form, a compound of formula (X) is especially useful for obtaining a compound of formula (X) from a mixture also comprising an acetal, especially an acetal of formula (XVI), more especially an acetal of formula (IV), or an acrylate, especially an acrylate of formula (XV), more especially an acrylate of formula (V), or a mixture of both an acetal and an acrylate.

In the acetal of formula (XVI) and the acrylate of formula (XV) the moiety $R^5$ is either an aryl (preferably phenyl), benzyl or a heteroaryl (preferably a pyridinyl, pyrimidinyl, pyrazinyl or triazinyl heterocycle) moiety which is optionally substituted by halogen (especially chlorine, fluorine or bromine), hydroxy, $S(O)_nR^6$ (wherein n is 0, 1 or 2, and $R^6$ is $C_{1-4}$ alkyl (especially methyl)), benzyl, phenoxy, or pyridinyloxy (wherein the last three are optionally substituted by halogen (especially chlorine or fluorine), cyano, $C_{1-4}$ alkyl, $C_{1-4}$ haloalkyl, $C_{1-4}$ alkoxy, $C_{1-4}$ haloalkoxy, $CSNH_2$, $CONH_2$ or nitro).

A compound of formula (X) in a substantially pure form is the compound more than 85% pure.

The immediately foregoing process is shown in Scheme II. In Scheme II, M and n are as defined above.

A compound of formula (XI) is prepared by contacting an aqueous solution of a base (preferably sodium hydroxide) and a mixture comprising a compound of formula (X) in a solvent (for example water or an inert hydrocarbon solvent such as xylene) at a suitable temperature, preferably at ambient temperature.

A compound of formula (XII) is prepared by contacting a compound of formula (XI) with an acid (organic acid (for example acetic acid) or preferably a mineral acid (for example hydrochloric acid)) in a suitable solvent (for example water) and at a suitable temperature (preferably ambient).

A compound of formula (X) is prepared by reacting a compound of formula (XII) with methanol in a suitable solvent (for example methanol) in the presence of an acid (preferably a strong mineral acid for example sulphuric acid or hydrochloric acid).

To prepare a compound of formula (X) in a substantially pure form, an aqueous base (preferably sodium hydroxide) is added to a mixture comprising a compound of formula (X) suspended in water and the resulting mixture is stirred and then filtered. An acid (preferably hydrochloric acid) is then added to the filtrate and a solid product forms which is collected by filtration and may be dried. The solid product is heated at reflux in methanol and in the presence of a strong acid (for example sulphuric acid). Evaporation of the solvent leaves a compound of formula (X) in a substantially pure form. The purity may be increased by crystallisation (from, for example, methanol).

The present invention also provides a process for the preparation of a compound of general formula (XI), and stereoisomers thereof, wherein M is an alkali metal, and n is 1, which comprises bringing together a compound of formula (XIII), an alkali metal alkoxide and an alkyl formate in tetrahydrofuran, at a suitable temperature (preferably in the range −20° to 100° C., more preferably in the range −10° to 50° C., for example 0° to 30° C.).

In one particular aspect the present invention provides a process for the preparation of a compound of formula (XII), and stereoisomers thereof, comprising the steps of:

a) bringing together a compound of formula (XIII), an alkali metal alkoxide and an alkyl formate in tetrahydrofuran, at a suitable temperature (preferably in the range −20° to 100° C., more preferably in the range −10° to 50° C., for example 0° to 30° C.); and b) contacting the product so formed with a suitable acid.

The alkali metal moiety of the alkali metal alkoxide is, for example, potassium but is preferably sodium.

The alkyl moiety of the alkyl formate and the alkali metal alkoxide are preferably a straight or branched chains containing from one to four carbon atoms. For example, they are independently, methyl, ethyl, n-propyl, iso-propyl, n-butyl or tert-butyl.

To prepare a compound of general formula (XII), the process of the invention is conveniently carried out by adding benzofuran-2(3H)-one to a mixture of an alkali metal alkoxide (preferably sodium methoxide) in tetrahydrofuran and then adding a solution of an alkyl formate (preferably methyl formate) in tetrahydrofuran. After a suitable time, the reaction mixture is added to water and the solution is acidified and extracted with an organic solvent (for example, dichloromethane). The extracts are combined, washed with water and the organic solvent is removed by distillation, to leave the crude product.

EXAMPLES

The following Examples, other than Example 15, illustrate the invention. Example 15 is included to illustrate a process of the invention by analogy. All reactions were performed under an atmosphere of nitrogen.

Where shown, NMR data are selective; no attempt is made to list every signal. The following abbreviations are used throughout:

mpt=melting point  brs=broad singlet
s=singlet  gc=gas chromatography
d=doublet  m=multiplet
t=triplet  MS=mass spectrum

Example 1

This Example illustrates a preparation of 3-(α-methoxy) methylenebenzofuran-2(3H)-one.

Benzofuran-2(3H)-one (10.2 g), acetic anhydride (30 cm$^3$) and trimethyl orthoformate (12.1 g) were stirred at 100°–105° C. for 12 hours. During this time, low boiling point liquids were collected using a Dean and Stark apparatus.

The reaction mixture was allowed to cool and was concentrated under reduced pressure (using a water bath temperature of 60° C.) to give a brown solid. This was dissolved in dichloromethane (1000 cm$^3$) and this solution was washed with water (2×50 cm$^3$) and concentrated under reduced pressure (using a water bath temperature of 60° C.) to give a crude product (13.5 g). Some of this crude product was added to crude product from similar experiments, and the total crude product was taken up in methanol and treated with activated carbon. After this, the methanolic solution was refluxed for 30 minutes, cooled to below 10° C., filtered and the residue was washed with cold methanol. The residue was dried at 50° C. under vacuum to give an off-white solid with a mpt of 102°–103° C.

The product from a similar experiment gave the following physical data: $^1$H NMR (CDCl$_3$, 250 MHz): δ 7.6(1H,s); 7.6–7.1(4H,m); 4.15(3H,s) ppm. $^{13}$C NMR (CDCl$_3$, 62.9 MHz): δ 169.9, 160.1, 152.0, 128.3, 123.9, 123.0, 122.8, 110.4, 103.9, 63.9 ppm. MS: molecular ion m/z 176.

Example 2

This Example illustrates an alternative preparation of 3-(α-methoxy)-methylenebenzofuran-2(3H)-one.

o-Hydroxyphenylacetic acid (15.2 g), toluene (95 cm$^3$) and glacial acetic acid (5 cm$^3$) were mixed and heated to reflux for 4 hours, after which time there was no undissolved starting material. During this time water (2.2 ml) was collected in a Dean and Stark apparatus. The reaction mixture was then cooled and allowed to stand overnight.

Acetic anhydride (40 cm$^3$) was then added to the reaction mixture and the low boiling solvents (mostly toluene) (100 cm$^3$) were distilled off. After cooling to below 50° C., trimethyl orthoformate (15.9 g) was added to the reaction mixture which was then heated to 100°–105° C. for 20 hours. Analysis by gas chromatography showed that about 5% of starting material remained.

The reaction mixture was worked-up and purified as in Example 1.

Example 3

This Example illustrates an alternative preparation of 3-(α-methoxy)-methylenebenzofuran-2(3H)-one.

Benzofuran-2(3H)-one (10 g), o-hydroxyphenylacetic acid (11.3 g), acetic anhydride (60 cm$^3$) and trimethyl orthoformate (23.7 g) were heated to 100°–105° C. for 14 hours. During this time some volatile products were collected in a Dean and Stark apparatus. Analysis of the reaction mixture showed that there was still about 5% of starting material present.

The reaction mixture was concentrated under reduced pressure (water bath at 70° C.) to give a crude product (28.24 g). This was combined with crude product from a similar experiment and recrystallised from methanol to give the title compound.

Example 4

This Example illustrates a preparation of compound (I) wherein R$^1$, R$^2$, R$^3$ and R$^4$ are all hydrogen, Z$^1$ is chlorine and W is (CH$_3$O)$_2$CHCHCO$_2$CH$_3$.

(α-Methoxy)methylenebenzofuran-2(3H)-one (8.8 g) was dissolved in tetrahydrofuran (100 ml). To this were added sodium methoxide (2.78 g) and methanol (1.6 g). On addition the reaction mixture turned red and there was an exotherm (reaction mixture went from 20° C. to 45° C.). The reaction mixture was cooled to 20° C., stirred for 15 minutes, 4,6-dichloropyrimidine (7.45 g) was added and it was stirred for 22 hours. The reaction mixture was then filtered and the residue was washed with dichloromethane (50 ml). The filtrate and washings were combined and evaporated under reduced pressure using a water bath temperature of 30° C. to leave an orange oil. This was dissolved in dichloromethane (200 ml) to which water (100 ml) was added. The mixture was shaken, the water layer was neutralised with concentrated hydrochloric acid and the organic layer was separated and evaporated under reduced pressure (using a water bath temperature of 50° C.) to leave a viscous cloudy orange oil (15.66 g). Proton NMR showed that this comprised mainly a compound of formula (I) wherein Z$^1$ is chlorine, W is (CH$_3$O)$_2$ CHCHCO$_2$CH$_3$, X is oxygen and R$^1$, R$^2$, R$^3$ and R$^4$ are hydrogen.

The product from a similar experiment gave the following physical data: $^1$H NMR (CDCl$_3$): δ 8.6(1H,s); 7.7–7.1(4H, m); 6.9(1H,s); 5.0(1H,d); 4.2(1H,d); 3.55(3H,s); 3.4(3H,s); 3.2(3H,s) ppm. $^{13}$C NMR (CDCl$_3$): δ 170.8, 170.4, 162.0, 158.4, 150.2, 130.0, 129.1, 127.3, 126.7, 122.4, 107.9, 104.8, 55.5, 53.6, 52.2, 48.0 ppm.

Example 5

This Example illustrates a preparation of the (E)-isomer of a compound of formula (I) wherein R$^1$, R$^2$, R$^3$ and R$^4$ are hydrogen, Z$^1$ is chlorine and W is CH$_3$O.CH=CCO$_2$CH$_3$.

A small amount of the viscous cloudy orange oil (prepared in Example 4) was heated to 250° C. for 30 minutes with a catalytic amount of potassium bisulphate. On cooling, the reaction mixture was dissolved in dichloromethane (50 ml) and this was washed with water (50 ml). The organic layer was separated and evaporated under reduced pressure (using a water bath temperature of 60° C.) to leave a residue.

The product from a similar experiment gave the following physical data: $^1$H NMR (CDCl$_3$): δ 8.6(1H,s); 7.5(1H,s); 7.5–7.1(4H,m); 6.8(1H,s); 3.7(3H,s); 3.6(3H,s) ppm. $^{13}$C NMR (CDCl$_3$, 62.9 MHz): δ 170.6, 167.5, 162.1, 160.9, 155.8, 150.2, 133.1, 129.6, 126.5, 126.3, 122.2, 107.6, 107.3, 62.3, 51.9 ppm.

Example 6

This Example illustrates an alternative preparation of the (E)-isomer of a compound of formula (I) wherein R$^1$, R$^2$, R$^3$ and R$^4$ are all hydrogen, Z$^1$ is chlorine and W is CH$_3$O.CH=CCO$_2$CH$_3$.

Sodium methoxide (2.84 g) was suspended in methyl acetate (30 ml) and methanol (1.6 g) and the suspension was cooled to 0°–5° C. (α-Methoxy)-methylenebenzofuran-2 (3H)-one (8.8 g) was added portionwise to the suspension over one minute to keep the temperature below 20° C. The reaction mixture was allowed to warm to room temperature and 4,6-dichloropyrimidine (7.45 g) was added. The reaction mixture was stirred at 20°–25° C. for 19 hours (approximately). The reaction mixture was cooled to 0°–5°

C. and further charges of sodium methoxide (1.0 g), methanol (0.56 g) and 4,6-dichloropyrimidine (2.61 g) were added to it. The reaction mixture was stirred at room temperature for 23 hours.

The reaction mixture was then filtered and the residue washed with methyl acetate (2×20 ml). The filtrate and washings were combined and evaporated under reduced pressure (using a water bath temperature of 60° C. and for a period long enough to remove volatile pyrimidine residues) to give a viscous, cloudy, red oil (17.02 g).

This oil was then heated at 160° C. at 20 mm Hg for 1 hour using a Kugelrohr apparatus. After this time potassium bisulphate (0.16 g) was added to the oil and the oil was kept at 160° C. at 20 mm Hg for 2 hours. The oil was cooled, dissolved in dichloromethane (100 ml) and this solution was washed with water (100 ml) containing 36% hydrochloric acid (1 cm$^3$). The organic layer was separated and evaporated under reduced pressure (using a water bath temperature of 30° C.) to leave an oil. This oil was heated at 180° C. at 20 mm Hg for 3 hours. Analysis showed the viscous red tar (12.11 g) remaining to be crude compound (VII) and this was used directly for the next stage (Example 7).

Example 7

This Example illustrates the preparation of a compound of formula (VI) wherein $R^1$, $R^2$, $R^3$ and $R^4$ are all hydrogen; Z is hydrogen, Y is 2-cyano and the isomer is the (E)-isomer.

The compound prepared in Example 6 (12.11 g), 2-cyanophenol (4.15 g), potassium carbonate (6.9 g), cuprous chloride (0.11 g) and N,N-dimethylformamide (83 cm$^3$) were mixed together and heated at 120° C. for 90 minutes. The reaction mixture was then filtered and the residue was washed with N,N-dimethylformamide (20 ml). The filtrate and washings were combined and evaporated under reduced pressure (using a water bath at 70° C.) to leave a crude product (15.87 g).

The crude product was dissolved in methanol (16 ml) at reflux, then cooled to 0°–5° C.; the crystals formed were filtered off, washed with 60–80 petroleum ether (2×10 ml) and dried in a vacuum oven at 50° C. to leave a dark brown solid (8.71 g).

The product from a similar experiment gave the following physical data: $^1$H NMR (CDCl$_3$): δ 8.4(1H,s); 7.6–7.8 (2H,m); 7.5(1H,s); 7.2–7.5(6H,m); 6.4(1H,s); 3.7(3H,s); 3.6 (3H,s) ppm.

Example 8

This Example illustrates an alternative preparation of the (E)-isomer of a compound of general formula (I) wherein $R^1$, $R^2$, $R^3$ and $R^4$ are all hydrogen, $Z^1$ is chlorine and W is CH$_3$O.CH=CCO$_2$CH$_3$.

Crude compound (I) (wherein $Z^1$ is chlorine, W is (CH$_3$O)$_2$CHCHCO$_2$CH$_3$, X is oxygen and $R^1$, $R^2$, $R^3$ and $R^4$ are all hydrogen) (18.03 g) (prepared by a method involving an acidic work-up) was heated at 160° C. and at 10 mm Hg using a Kugelrohr apparatus for 4 hours. The title compound was obtained as a very viscous red oil (13.82 g).

Example 9

This Example illustrates an alternative preparation of 3-(α-methoxy)-methylenebenzofuran-2(3H)-one.

Trimethyl orthoformate (7.95 g), iso-butyric anhydride (25 cm$^3$) and o-hydroxyphenylacetic acid (7.6 g) were mixed and heated to 100° C. for 19 hours. During this time low boiling point liquids were collected using a Dean and Stark apparatus.

The reaction mixture was then concentrated under reduced pressure (using a water bath temperature of 85° C.) to leave a black oil (8.64 g). The black oil was taken up in hot methanol (20 ml) and on cooling this solution gave the title compound as a crystalline product (4.16 g).

Example 10

This Example illustrates an alternative preparation of the compound of formula (VI) wherein Z is hydrogen, Y is 2-cyano, and $R^1$, $R^2$, $R^3$ and $R^4$ are hydrogen, and the isomer is the (E)-isomer.

Crude compound (I) (wherein X is oxygen; $R^1$, $R^2$, $R^3$ and $R^4$ are all hydrogen; $Z^1$ is chlorine and W is (CH$_3$O)$_2$CHCHCO$_2$CH$_3$) (14.47 g) (prepared in a method analogous to that of Example 4), 2-cyanophenol (4.26 g), potassium carbonate (7.05 g), cuprous chloride (0.12 g) and N,N-dimethylformamide (85 ml) were mixed together and heated to 120° C. for 90 minutes. The reaction mixture was cooled to below 30° C., filtered and the residue washed with N,N-dimethylformamide (20 ml). The filtrate and washings were combined and concentrated under reduced pressure (using a water bath temperature of 80° C.) to remove the N,N-dimethylformamide.

The resulting black oil was dissolved in hot methanol (15 ml). Some crystals of product formed after allowing the solution to stand at room temperature for 3 weeks. The $^1$H NMR of this product was the same as to that given in Example 7.

Example 11

This Example illustrates an alternative preparation of the (E)-isomer of a compound of general formula (I) wherein $R^1$, $R^2$, $R^3$ and $R^4$ are all hydrogen; $Z^1$ is chlorine and W is CH$_3$O.CH=CCO$_2$CH$_3$.

Sodium methoxide (6.25 g, 0.11 moles), methyl acetate (100 ml) and methanol (3.52 g, 0.11 moles) were charged to a 250 ml flask under nitrogen and were cooled to 0°–5° C. 3-(α-Methoxy)methylenebenzofuran-2(3H)-one (21.12 g, 0.12 moles) was added to this mixture keeping the temperature below 10° C. and once the addition was complete the reaction mixture was allowed to warm to room temperature.

4,6-Dichloropyrimidine (15.05 g, 0.10 moles) was then added to the reaction mixture and the reaction mixture was stirred overnight (approximately 20 hours) at 20°–25° C. and then allowed to stand over the weekend.

The reaction mixture was evaporated on a rotary evaporator at 40° C. and to leave a red oil. The red oil was dissolved in toluene (200 ml) and filtered through charcoal, the charcoal being washed with further toluene (50 ml). The toluene solution and washings were combined, washed with water (200 ml) and evaporated on a rotary evaporator at 60° C. to leave a viscous red oil (33.15 g).

Some of the viscous red oil (23.15 g) was heated with potassium bisulphate (0.14 g) at 120°–130° C. at 12 mm Hg for one hour. This mixture was cooled to 80° C. and dissolved in toluene (150 ml). The toluene solution was washed with water (150 ml) and then evaporated on a rotary evaporator at 75° C. to leave a crude product (20.51 g).

Crystallisation of the crude product from iso-propyl acetate (25 ml) gave the title compound (10.6 g, mpt 104°–6° C.). $^1$H NMR (CDCl$_3$, 250 MHz): δ 8.6(1H,s); 7.5(1H,s); 7.5–7.1(4H,m); 6.8(1H,s); 3.7(3H,s); 3.6(3H,s) ppm.

Example 12

This Example illustrates the preparation of a compound of formula (I) where $R^1$, $R^2$, $R^3$ and $R^4$ are all hydrogen; Z is chlorine and W is $CH_3O.CH=CCO_2CH_3$.

Sodium methoxide (2.97 g, 0.055 moles) and acetonitrile (19.60 g) were charged to a flask at ambient temperature and (α-methoxy)-methylenebenzofuran-2(3H)-one (11.40 g, 0.065 moles) was added over 2 minutes, causing the temperature of the reaction mixture to increase to about 40° C. The reaction mixture was cooled to ambient temperature and 4,6-dichloropyrimidine (7.45 g, 0.05 moles) was added to give a red-brown solution, which was heated at 60° C. for 6.25 hours. The solvent was distilled out at 60° C./15 mm Hg pressure to leave a red semi-solid product (21.85 g). Gas chromatographic analysis of the product indicated the title compound at about 55% strength and a compound of formula (I) (wherein X is oxygen; $R^1$, $R^2$, $R^3$ and $R^4$ are all hydrogen, $Z^1$ is chlorine and W is $(CH_3O)_2CHCHCO_2CH_3$) at about 2.5% strength.

The crude product was crystallised using iso-propyl acetate to give the title compound as a solid product (mpt 103°–105° C.) which was pure by gas chromatographic analysis.

The solid product gave the following physical data: $^1$H NMR (CDCl$_3$, 250 MHz): δ 8.6(1H,s); 7.5(1H,s); 7.2–7.5 (4H,m); 6.8(1H,s); 3.7(3H,s); 3.6(3H,s) ppm. $^{13}$C NMR (CDCl$_3$, 62.9 MHz): δ 8 170.3, 167.2, 161.8, 160.6, 158.5, 149.9, 132.8, 129.2, 126.1, 125.9, 121.9, 107.2, 106.9, 61.9, 51.5 ppm. Mass spectroscopy showed a molecular ion at m/z 320.

Example 13

This Example illustrates the preparation of 3-((α-methoxy)methylene)-5-chloro-benzofuran-2(3H)-one.

5-Chloro-benzofuran-2(3H)-one (4 g, 0.02M), acetic anhydride (16.7 g, 0.16M) and trimethyl orthoformate (4.24 g, 0.04M) were heated to 100° C. for 2 hours. After this time the reaction mixture was cooled to 20° C. and then concentrated under reduced pressure (water bath at 70° C.) to leave a crude product as a dark red tar (3.7 g).

The tar was dissolved in hot methanol (5 ml) and the resulting solution was allowed to cool. A solid crystallised out of this solution.

The above procedure of dissolving crude product in hot methanol and then harvesting crystalline solid was repeated twice to give the title compound as a fawn solid (0.3 g) with a melting point of 128°–130° C. $^1$H NMR (CDCl$_3$, 250 MHz): δ 7.6(1H,s); 7.6–7.0(3H,m); 4.2(3H,s) ppm.

Example 14

This Example illustrates the preparation of 3-((α-methoxy)methylene)-5-acetoxy-benzofurzan-2(3H)-one.

Acetic anhydride (25 ml) and 5-hydroxy-benzofuran-2 (3H)-one (1 g, 0.0067M) were stirred at room temperature, under a nitrogen atmosphere, for 10 minutes. After this time trimethyl orthoformate (1.06 g, 0.01M) was added and the resulting reaction mixture was heated at 100° C. (±5° C.) for 12 hours. The reaction mixture was then allowed to cool to room temperature and a pink solid separated out of the mixture.

The reaction mixture was concentrated under reduced pressure (water bath at 70° C.) to leave a residue comprising a pink solid. The pink solid was dissolved in dichloromethane (50 ml) and the resulting solution was washed with cold water (50 ml). The organic layer was then concentrated under reduced pressure (water bath at 70° C.) to leave the title compound in the form of pink needle shaped crystals (1.15 g) with a melting point of 206°–210° C. $^1$H NMR (CDCl$_3$, 250 MHz): δ 7.6(1H,s); 7.4–6.9(3H,m); 4.2(3H,s); 2.3(3H,s) ppm. $^{13}$C NMR (CDCl$_3$, 100.6 MHz) δ 169.8, 169.5, 160.7, 149.0, 146.6, 123.2, 121.0, 116.3, 110.6, 103.4, 63.8, 21.1 ppm.

Example 15

This Example illustrates an alternative preparation of 3-(α-ethoxy)-methylenebenzofuran-2(3H)-one.

Benzofuran-2(3H)-one (6.7 g, 0.05M) was dissolved in toluene (40 g), under a blanket of nitrogen, at 20°–25° C. Diethoxymethyl acetate (12.15 g, 0.075M) was added and the reaction solution was heated at 100°–105° C., with distillative removal of low boiling by-products, for 28 hours. Toluene and unreacted diethoxymethyl acetate were distilled to leave a yellow solid product (9.53 g) which was crystallized from methanol and dried at 50° C. to give the title compound as a solid with a mpt of 101°–102° C. $^1$H NMR (CDCl$_3$, 250 MHz): δ 1.5(3H,t); 4.4(2H,q); 7.1–7.6(4H,m); 7.7(1H,s) ppm. $^{13}$C NMR (CDCl$_3$, 62.9 MHz): δ 169.8, 158.9, 151.5, 127.8, 123.6, 122.7, 122.7, 110.0, 103.2, 72.8, 15.4 ppm. MS: molecular ion m/z 190.

Example 16

This Example illustrates the preparation of 3-formylbenzofuran-2(3H)-one.

A mixture of tetrahydrofuran (20 g) and sodium methoxide (4.05 g, 0.075M), under a blanket of nitrogen, was cooled to 15° C. Benzofuran-2(3H)-one (6.7g, 0.05M) was added over 5 minutes whilst maintaining the reaction temperature below 30° C. The mixture was cooled to 15°–20° C. and a solution of methyl formate (3.9 g, 0.065M) in tetrahydrofuran (5 g) was added over 2 hours and the reaction mixture was then stirred for 16 hours. The resulting yellow suspension was added to water (50 g) and the solution was acidified to about pH4 using 36% hydrochloric acid. The title compound was extracted with dichloromethane (2×65 g). The extracts were combined and washed with water (50 g). Distillation of the dichloromethane afforded a product, in a crude state, as a waxy solid (7.41 g).

Confirmation that the product of this Example was 3-formylbenzofuran-2(3H)-one was done by comparing the liquid chromatographs of the product of this Example with that of a previously prepared and analysed sample of 3-formylbenzofuran-2(3H)-one.

Example 17

The preparation of 3-(α-hydroxy)methylenebenzofuran-2 (3H)-one from 3-(α-methoxy)methylenebenzofuran-2(3H)-one.

47% Aqueous sodium hydroxide solution (4.5 g, 0.05 mole) was added to a suspension of 3-(α-methoxy) methylenebenzofuran-2(3H)-one (8.8 g, 0.05 mole) in water (50 g). The reaction mixture was stirred at ambient temperature for 2 hours and acidified to about pH4 with 36% hydrochloric acid. A solid was collected by filtration, washed with water and dried at 50° C. to give the title compound (7.8 g, mpt=168°–170° C.). $^1$H NMR (CDCl$_3$, 250 MHz): δ 8.1(1H,s), 7.6(1H,d), 7.1–7.3(3H,m) ppm.

Example 18

The preparation of the sodium salt of 3-(α-hydroxy)methylenebenzofuran-2(3H)-one form 3-(α-methoxy)methylenebenzofuran-2(3H)-one.

47% Aqueous sodium hydroxide solution (4.5 g, 0.05 mole) was added to a suspension of 3-(α-methoxy)methylenebenzofuran-2(3H)-one (8.8 g, 0.05 mole) in water (50 g). The reaction mixture was stirred at ambient temperature for 2 hours after which a solid was collected by filtration. The solid was washed with tetrahydrofuran (10 g) and dried at 50° C. to give the title compound (7.1 g, mpt=>300° C.). $^1$H NMR (DMSO, 250 MHz): δ 9.4(1H,s), 7.5(1H,d), 6.7–7.0(3H,m) ppm; $^{13}$C NMR (DMSO, 62.9 MHz): δ 178.3, 172.7, 147.6, 129.8, 121.7, 119.6, 117.3, 107.6, 91.2 ppm.

Example 19

The preparation of the potassium salt of 3-(α-hydroxy)methylenebenzofuran-2(3H)-one from 3-(α-methoxy)methylenebenzofuran-2(3H)-one.

85% Potassium hydroxide (1.73 g, 0.026 mole) was added to a suspension of 3-(α-methoxy)methylenebenzofuran-2(3H)-one (4.4 g, 0.025 mole) in water (100 g). The reaction mixture was stirred at ambient temperature for 2 hours. The water was distilled at 60° C., under a reduced pressure, to leave the title compound as a solid which was dried at 60° C. (4.7 g, mpt=>300° C.). $^1$H NMR (DMSO, 250 MHz): δ 9.3(1H,s), 7.5(1H,s), 6.6–6.9(3H,m) ppm. $^{13}$C NMR (DMSO, 62.9 MHz): δ 178.3, 172.7, 147.6, 129.8, 121.7, 119.5, 117.3, 107.6, 91.1 ppm.

Example 20

The preparation of 3-(α-hydroxy)methylenebenzofuran-2(3H)-one from its sodium salt.

36% Hydrochloric acid (4.0 g, 0.04 mole) was added to a suspension of the sodium salt of 3-(α-hydroxy)methylenebenzofuran-2(3H)-one (6.4 g, 0.035 mole) in water (50 g). The reaction mixture was stirred at ambient temperature for 1 hour after which time a solid was collected by filtration. The solid was washed with water (10 g) and dried at 50° C. to give the title compound (mpt=168°–170° C.). $^1$H NMR (DMSO, 250 MHz): δ 8.1(1H,s), 7.6(1H,d), 7.1–7.3(3H,m) ppm. $^{13}$C NMR (DMSO, 62.9 MHz): δ 169.7, 160.0, 150.5, 127.0, 123.8, 123.5, 122.0, 109.9, 100.4 ppm.

Example 21

The preparation of 3-(α-methoxy)methylenebenzofuran-2(3H)-one from 3-(α-hydroxy)methylenebenzofuran-2(3H)-one.

3-(α-Hydroxy)methylenebenzofuran-2(3H)-one (4.9 g, 0.03 mole) was heated at reflux in methanol, which contained a drop of 98% sulphuric acid, for 5 hours. The solvent was distilled at 60° C., under a reduced pressure, to leave a residue (5.3 g) which was identified as the title compound by comparing the gas chromatographs of the residue and a previously prepared sample of the title compound (mpt (crystals from methanol)=102°–103° C.). $^1$H NMR (CDCl$_3$, 250 MHz): δ 7.6(1H,s), 7.6(1H,d), 7.1–7.3(3H,m), 4.2(3H,s) ppm.

Example 22

The recovery of 3-(α-methoxy)methylenebenzofuran-2(3H)-one from a mixture of chemical compounds, via isolated 3-(α-hydroxy)methylenebenzofuran-2(3H)-one.

47% Aqueous sodium hydroxide (0.56 g, 0.007 mole) was added to 3-(α-methoxy)methylenebenzofuran-2(3H)-one (1.1 g, 0.007 mole), contained in mixture of chemical compounds, suspended in water (200 g). The reaction mixture was stirred for 3 hours at ambient temperature and filtered. The filtrates were acidified to about pH4 with 36% hydrochloric acid and the solid product was filtered and dried at 60° C. The solid product (0.8 g) was heated at reflux in methanol, which contained a drop of 98% sulphuric acid, for 4 hours. The solvent was distilled at 400° C., under reduced pressure, to leave the title compound (0.9 g) as a solid (mpt (crystals from methanol)=102°–103° C). $^1$H NMR (CDCl$_3$, 250 MHz): δ 7.6(1H,s), 7.6(1H,d), 7.1–7.3(3H,m), 4.2(3H,s) ppm.

Example 23

The recovery of 3-(α-methoxy)methylenebenzofuran-2(3H)-one from a mixture of chemical compounds, via isolated sodium salt of 3-(α-hydroxy)-methylenebenzofuran-2(3H)-one.

47% Aqueous sodium hydroxide (8.5 g. 0.1 mole) was added to 3-(α-methoxy)methylenebenzofuran-2(3H)-one, contained in a mixture of chemical compounds, in xylene (20 g). The reaction mixture was stirred at ambient temperature for 24 hours and the product collected by filtration. The solid product was washed with water (10 g) and xylene (8 g) and dried. The product (10 g) was slurried in water (50 g) and acidified to about pH1 with 36% hydrochloric acid. The product was collected by filtration and dried. The product (7.5 g) was heated at reflux in methanol (40 g), which contained a drop of 98% sulphuric acid, for 8 hours. By distilling the solvent under a reduced pressure the title product was isolated. (mpt (crystals from methanol)= 102°–103° C.). $^1$H NMR (CDCl$_3$, 250 MHz): δ 7.6(1H,s), 7.6(1H,d), 7.1–7.3(3H,m), 4.2(3H,s) ppm.

Example 24

The preparation of the calcium salt of 3-(α-hydroxy)methylenebenzofuran-2(3H)-one from 3-(α-methoxy)methylenebenzofuran-2(3H)-one. 3-(α-methoxy)methylenebenzofuran-2(3H)-one (3.5 g, 0.02 mole) was added to calcium oxide (1.12 g, 0.02 mole) in water (750 g). The reaction mixture was stirred at ambient temperature for 3 hours after which time a solid was collected by filtration. The solid was washed with water (25 g) and dried at 50° C. to give the title compound (3.3 g, mpt=270° C. (decomposes)). $^1$H NMR (DMSO, 250 MHz): δ 9.2(1H,s), 7.5(1H,d), 6.7–7.0(3H,m) ppm.

Example 25

The preparation of 3-(α-hydroxy)methylenebenzofuran-2(3H)-one from its calcium salt.

36% Hydrochloric acid (2.0 g) was added to a suspension of the calcium salt of 3-(α-hydroxy)methylenebenzofuran-2(3H)-one (3 g, 0.015 mole) in water (25 g). The reaction mixture was stirred at ambient temperature for 2 hours after which time a solid was collected by filtration. The solid was washed with water (10 g) and dried at 50° C. to give the title compound (2.3 g, mpt=169°–171° C.). $^1$H NMR (DMSO, 250 MHz): δ 8.1(1H,s), 7.6(1H,d), 7.1–7.3(3H,m) ppm.

Example 26

This Example illustrates the preparation of a compound of formula (V), wherein $Z^1$ is chlorine.

A toluene solution containing a compound of formula (V) (wherein $Z^1$ is chlorine, 1.08 g) and a compound of formula (IV) (wherein $Z^1$ is chlorine, 5.68 g) was treated with para-toluenesulphonic acid (0.285 g). The mixture was heated at 85°–90° C. for 5 hours, under a vacuum of 130–220 mm Hg to distill the methanol formed in the reaction. The toluene was then distilled at 80° C. under a vacuum of 15 mm Hg to afford the product, which was analysed by liquid chromatography against a known standard sample, and shown to contain the title compound (6.23 g).

Preparations of compounds of formulae (I) wherein W is $(CH_3O)_2CHCHCO_2CH_3$ (A) or $CH_3O.CH=CCO_2CH_3$ (B); X is oxygen; $R^1$, $R^2$, $R^3$ and $R^4$ are all hydrogen; and $Z^1$ is chlorine, are listed in Table I. The conditions under which the preparations were conducted and their results are also shown in Table I.

In Table I the following abbreviations are used:
gc=Gas chromatography
NaOMe=Sodium methoxide
DCP=4,6-dichloropyrimidine
FUR=3-(α-methoxy)methylenebenzofuran-2(3H)-one
MeOH=Methanol
MeAc=Methyl acetate
Xyl=Xylene
Tol=Toluene
MeBut=Methyl butyrate
TButE=tert-Butyl ether
$CCl_4$=Carbon tetrachloride
DEM=Diethoxymethane
MIBK=Methylisobutyl ketone
THF=Tetrahydrofuran
DEE=Diethyl ether
ACN=Acetonitrile
Pyr=Pyridine

TABLE I

| Solvent | Molar Ratios | | | | | Product Ratios by gc area |
|---|---|---|---|---|---|---|
| | MeOH | FUR | NaOMe | DCP | T °C. | (A):(B) |
| MeOH | >10 | 1 | 2 | 2 | 20 | 97.0:3.0 |
| MeOH | >10 | 1 | 6 | 6 | 20 | 96.0:4.0 |
| MeAc | 4.4 | 1.3 | 1.2 | 1 | 20 | 92.3:7.7 |
| Xyl | 4.4 | 2 | 1.1 | 1 | 5 | 91.9:8.1 |
| Xyl | 4.4 | 2 | 1.1 | 1 | 20 | 91.8:8.2 |
| MeAc | 4.4 | 1.3 | 1.1 | 1 | 20 | 87.5:12.5 |
| Tol | 1 | 1 | 1 | 1 | 20 | 84.8:15.2 |
| McBut | 1 | 1 | 1 | 1 | 20 | 84.5:15.5 |
| TbutE | 1 | 1 | 1 | 1 | 20 | 82.5:17.5 |
| MeAc | 1.45 | 1 | 1.5 | 1.6 | 20 | 82.1:17.9 |
| MeOH | >10 | 1.3 | 1 | 1 | 20 | 81.8:18.2 |
| Xyl | 2 | 1.3 | 1.1 | 1 | 20 | 81.4:18.6 |
| MeAc | 1.1 | 1.3 | 1.1 | 1 | 20 | 81.1:18.9 |
| MeAc | 1.45 | 1 | 1.5 | 1.6 | 20 | 80.5:19.5 |
| MeAc | 1.45 | 1 | 1.5 | 1.6 | 20 | 80.4:19.6 |
| $CCl_4$ | 1 | 1 | 1 | 1 | 20 | 80.4:19.7 |
| DEM | 1 | 1 | 1 | 1 | 20 | 80.0:20.0 |
| MIBK | 1 | 1 | 1 | 1 | 20 | 79.5:20.5 |
| NeAc | 1 | 1 | 1 | 1 | 20 | 79.4:20.6 |
| THF | 8 | 1 | 2 | 2 | 20 | 79.0:21.0 |
| DEE | 1 | 1 | 1 | 1 | 20 | 78.2:21.8 |
| THF | 8 | 1 | 2 | 2 | 20 | 78.1:21.9 |
| THF | 1.3 | 1 | 1.3 | 1.3 | 20 | 77.5:22.5 |

TABLE I-continued

| Solvent | Molar Ratios | | | | | Product Ratios by gc area |
|---|---|---|---|---|---|---|
| | MeOH | FUR | NaOMe | DCP | T °C. | (A):(B) |
| MeAc | 1 | 1 | 1 | 1 | 20 | 77.5:22.5 |
| MeAc | 1 | 1 | 1 | 1 | 20 | 75.5:22.5 |
| Tol | 2 | 1.3 | 1.1 | 1 | 45 | 75.7:24.3 |
| THF | 1 | 1 | 1 | 1 | 20 | 75.6:24.4 |
| THF | 12 | 1 | 3 | 3 | 20 | 75.5:24.5 |
| MeAc | 1 | 1 | 1 | 1 | 20 | 75.5:24.5 |
| MeAc | 1.35 | 1 | 1.35 | 1.35 | 20 | 75.4:24.6 |
| THF | 1 | 1 | 1 | 1 | 20 | 75.2:24.8 |
| MeOH | >10 | 1 | 1 | 1 | 20 | 74.5:25.8 |
| ACN | 1 | 1 | 1 | 1 | 20 | 74.1:25.9 |
| THF | 0.9 | 1 | 0.9 | 0.9 | 20 | 72.1:27.9 |
| MeAc | 1.1 | 1.3 | 1.1 | 1 | 20 | 69.1:30.9 |
| THF | 1 | 1 | 1 | 1 | 50 | 61.5:38.5 |
| MeAc | 1 | 1.3 | 1.1 | 1 | 65 | 60.1:39.9 |
| Pyr | 1 | 1 | 1 | 1 | 20 | 45.2:54.8 |
| ACN | 1 | 1.3 | 1.1 | 1 | 65 | 43.1:56.9 |
| Tol | 1 | 1.3 | 1.1 | 1 | 60 | 41.9:58.1 |
| ACN | 1 | 1.3 | 1.1 | 1 | 45 | 32.7:67.3 |

CHEMICAL FORMULAE
(in description)

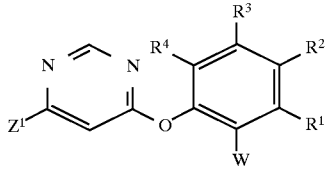

(I)

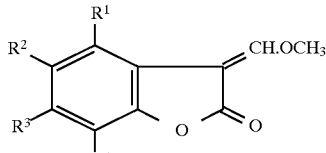

(II)

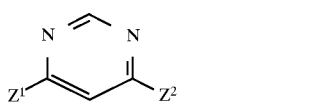

(III)

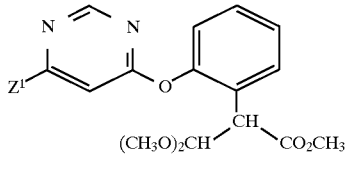

(IV)

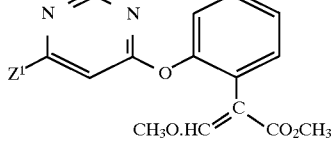

(V)

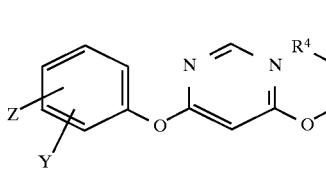

(VI)

-continued
CHEMICAL FORMULAE
(in description)
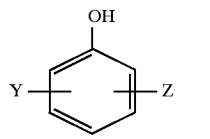 (VII)
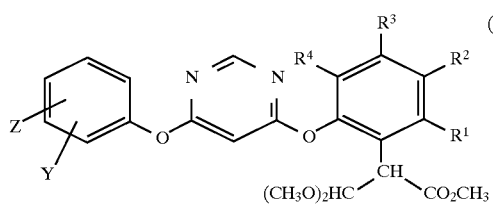 (VIII)
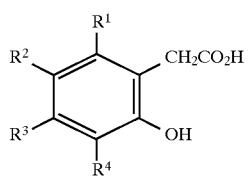 (IX)
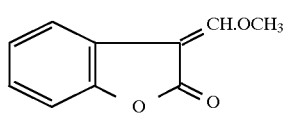 (X)
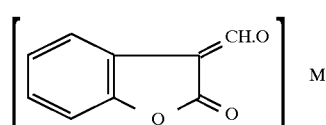 (XI)
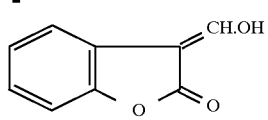 (XII)
-continued
CHEMICAL FORMULAE
(in description)
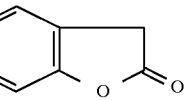 (XIII)
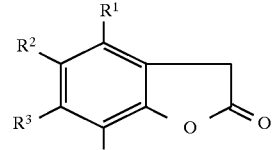 (XIV)
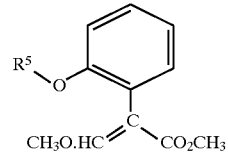 (XV)
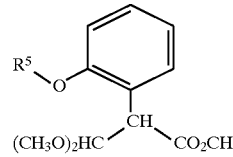 (XVI)
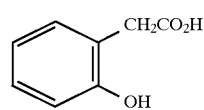 (XVII)
Scheme I
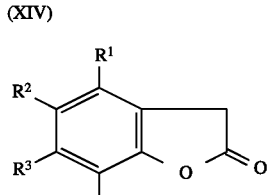 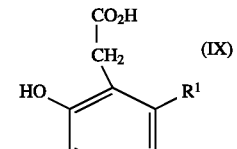
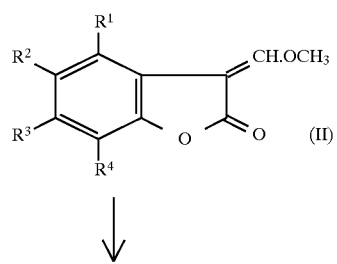

-continued
Scheme I

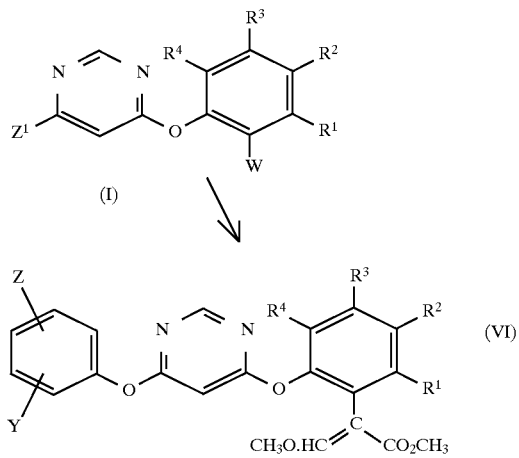

We claim:

1. A process for the preparation of a compound of formula (I):

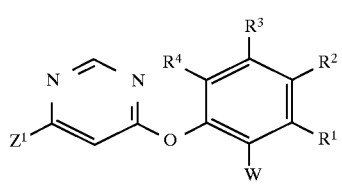

wherein W is $(CH_3O)_2CH.CHCO_2CH_3$ or $CH_3O.CH=CCO_2CH_3$; $Z^1$ is a halogen atom; and $R^1$, $R^2$, $R^3$ and $R^4$ are independently hydrogen, halogen, $C_{1-4}$ alkyl, $C_{1-4}$ alkoxy, acetoxy or acyl; the process comprising the steps of:

(a) reacting a compound of formula (II):

wherein $R^1$, $R^2$, $R^3$ and $R^4$ are as defined above, with a compound of formula $ROCH_3$, wherein R is a metal; and, (b) reacting the product of (a) with a compound of formula (III):

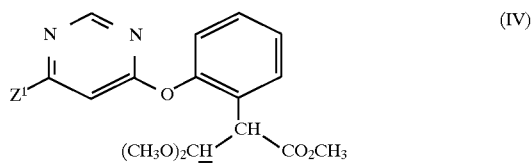

wherein $Z^1$ and $Z^2$ are halogen atoms.

2. A process for the preparation of a compound of general formula (IV):

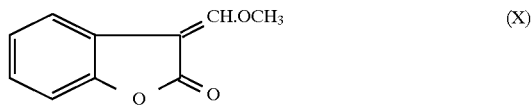

wherein $Z^1$ is a halogen atom; the process comprising reacting a compound of formula (X):

with a compound of general formula (III):

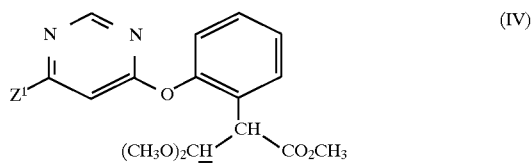

wherein $Z^1$ is as defined above and $Z^2$ is a halogen atom, in the presence of a methoxide anion.

3. A process for the preparation of a general formula (IV):

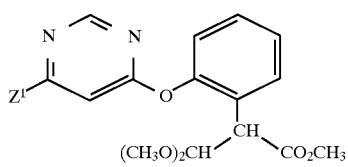

wherein $Z^1$ is a halogen atom; the process, which is carried out in the presence of methanol, comprising the steps of:

(a) reacting a compound of formula (X):

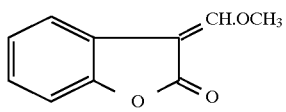

with a compound of formula $ROCH_3$, wherein R is a metal; and, (b) reacting the product of (a) with a compound of general formula (III):

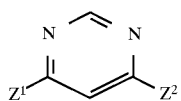

wherein $Z^1$ is as defined above, and $Z^2$ is a halogen atom.

4. A process for the preparation of a compound of general formula (V):

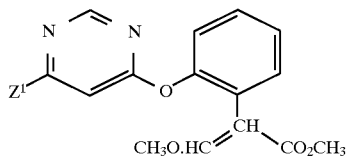

wherein $Z^1$ is a halogen atom; the process comprising the steps of:

a) reacting a compound of formula (X):

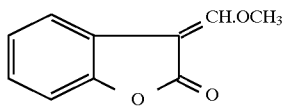

with a compound of formula ROCH wherein R is a metal; and b) reacting the product formed in (a) with a compound of general formula (III):

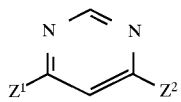

wherein $Z^1$ is as defined above and $Z^2$ is a halogen atom.

5. A process for the preparation of a compound of formula (I):

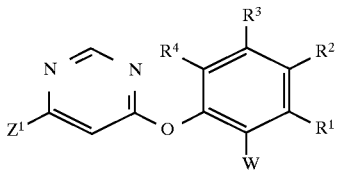

wherein W is $(CH_3O)_2CH.CHCO_2CH_3$ or $CH_3O.CH=CCO_2CH_3$; $Z^1$ is a halogen atom; and $R^1$, $R^2$, $R^3$ and $R^4$ are independently hydrogen, halogen, $C_{1-4}$ alkyl, $C_{1-4}$ alkoxy, acetoxy or acyl; the process comprising the steps of:

(a) reacting a compound of formula (II):

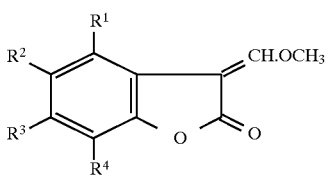

wherein $R^1$, $R^2$, $R^3$ and $R^4$ are as defined above, with a compound of formula $ROCH_3$, wherein R is a metal; and, (b) reacting the product of (a) with a compound of formula (III):

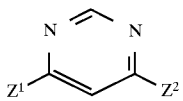

wherein $Z^1$ and $Z^2$ are halogen atoms; step (b) being carried out in the presence of methanol.

6. A process for the preparation of a compound of formula (VI):

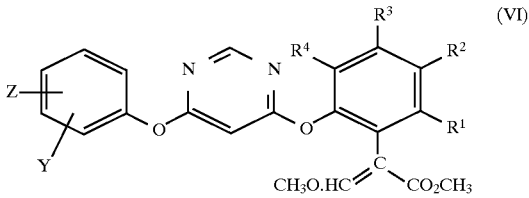

and stereoisomers thereof, wherein $R^1$, $R^2$, $R^3$ and $R^4$ are independently hydrogen, halogen, $C_1$–$C_4$ alkyl, $C_1$–$C_4$ alkoxy, acetoxy or acyl; and Y and Z are, independently, hydrogen, halogen, cyano, $C_{1-4}$ alkyl, $C_{1-4}$ haloalkyl, $C_{1-4}$ alkoxy, $C_{1-4}$ haloalkoxy, $CSNH_2$, $CONH_2$ or nitro; the process comprising the steps of:

a) reacting a compound of formula (II):

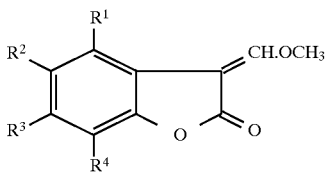

wherein $R^1$, $R^2$, $R^3$ and $R^4$ are as defined above; with a compound of formula $ROCH_3$ wherein R is a metal;

b) reacting the product of (a) with a compound of formula (III):

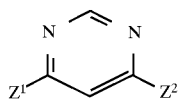

(III)

wherein $Z^1$ and $Z^2$ are halogen atoms; and 1) (c) eliminating methanol from the compound of formula (I);

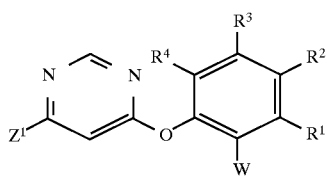

(I)

wherein $Z^1$ is a halogen atom: $R^1$, $R^2$, $R^3$ and $R^4$ are as defined above, and W is $(CH_3O)_2CHCHCO_2CH_3$, in the mixture of products from (b); and (d) reacting the product of (c) with a compound of formula (VII):

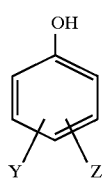

(VII)

wherein Z and Y are as defined above; or 2) (c) reacting the product of (b) with a compound of formula (VII):

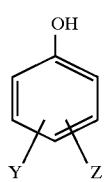

(VII)

wherein Z and Y are as defined above; and (d) (i) separating the compound of formula (VI); or
  (ii) eliminating methanol from the compound of formula (VIII):

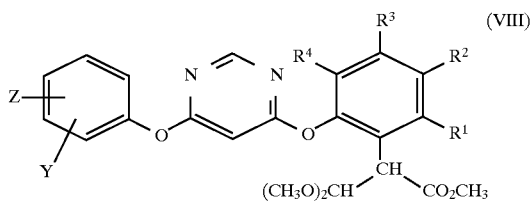

(VIII)

wherein $R^1$, $R^2$, $R^3$, $R^4$, Y and Z are as defined above, in the mixture of products from (c); or
  (iii) separating a compound of formula (VIII) from the mixture of products from (c) and eliminating methanol from it; or 3) (c) separating the compounds of formula (I), wherein W is $(CH_3O)_2CHCHCO_2CH_3$ and $CH_3O.CH=CCO_2CH_3$, in the mixture of products from (b); and (d) (i) reacting the compound of formula (I), wherein W is $CH_3O.CH=CCO_2CH_3$, with a compound of formula (VII);

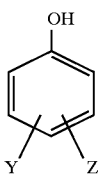

(VII)

wherein Y and Z are defined above; or
  (ii) reacting the compound of formula (I), wherein W is $(CH_3O)_2CHCHCO_2CH_3$, with a compound of formula (VII):

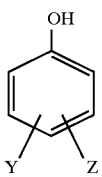

(VII)

and eliminating methanol from the product so formed; or
  (iii) eliminating methanol from the compound of formula (I), wherein W is $(CH_3O)_2CHCHCO_2CH_3$, and reacting the product so formed with a compound of formula (VII):

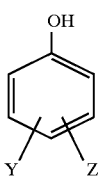

(VII)

wherein Y and Z are as defined above.

7. A process as claimed in claim 1 wherein steps (a) and (b) are carried out in the presence of methanol.

8. A process for the preparation of a compound of formula (I):

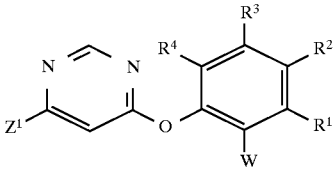

(I)

wherein W is $(CH_3O)_2CH.CHCO_2CH_3$ or $CH_3O.CH=CCO_2CH_3$; $Z^1$ is a halogen atom; and $R^1$, $R^2$, $R^3$ and $R^4$ are independently hydrogen, $C_1-C_4$ alkyl, $C_{1-4}$ alkoxy, acetoxy or acyl; the process comprising the steps of:

i) (a) reacting a compound of formula (XWV):

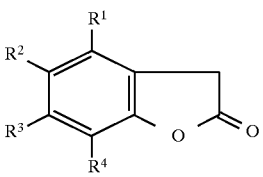

(XIV)

wherein $R^1$, $R^2$, $R^3$ and $R^4$ are as defined above, with trimethyl orthoformate;
  (b) reacting the product of step (a) with a compound of formula $ROCH_3$, wherein R is a metal; and,
  (c) reacting the product of step (b) with a compound of formula (III):

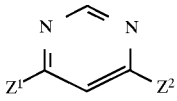

wherein $Z^1$ and $Z^2$ are halogen atoms; or ii) (a) reacting a compound of formula (XIV):

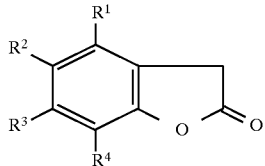

wherein $R^1$, $R^2$, $R^3$ and $R^4$ are as defined above, with a dimethoxymethyl carboxylate;

(b) reacting the product of step (a) with a compound of formula $ROCH_3$, wherein R is a mental; and, (c) reacting the product of step (b) with a compound of formula (III); or iii) (a) cyclising a compound of formula (IX):

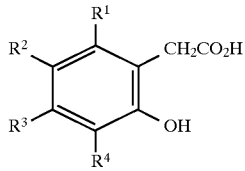

wherein $R^1$, $R^2$, $R^3$ and $R^4$ are as defined above, and reacting the product formed with either trimethyl orthofornate or a dimethoxymethyl carboxylate;

(b) reacting the product of step (a) with a compound of formula $ROCH_3$, wherein R is a metal; and, (c) reacting the product of step (b) with a compound of formula (III).

9. A process as claimed in claim 8 wherein steps (b) and (c) are carried out in the presence of methanol.

10. A process as claimed in claim 1 wherein $R^1$, $R^2$, $R^3$ and $R^4$ are all hydrogen.

11. A process in accordance with claim 1 wherein R is an alkali metal.

12. A process as claimed in claim 6 wherein steps (a) and (b) are carried out in the presence of methanol.

13. A process as claimed in claim 6 wherein $R^1$, $R^2$, $R^3$ and $R^4$ are hydrogen.

14. A process as claimed in claim 6 wherein R is an alkali metal.

15. A process as claimed in claim 8 wherein $R^1$ $R^2$ $R^3$ and $R^4$ are all hydrogen.

16. A process as claimed in claim 8 wherein R is an alkali metal.

* * * * *